United States Patent
Konstantino et al.

(10) Patent No.: US 10,232,148 B2
(45) Date of Patent: Mar. 19, 2019

(54) BALLOON CATHETER SYSTEM AND METHOD OF USING SAME

(71) Applicant: Quattro Vascular Pte Ltd., Singapore (SG)

(72) Inventors: Eitan Konstantino, Orinda, CA (US); Tanhum Feld, Moshav Merhavya (IL); Gary Binyamin, Berkeley, CA (US); Jayson Delos Santos, Pinole, CA (US); Nadia Matov, San Jose, CA (US); Guillermo Piva, San Ramon, CA (US)

(73) Assignee: TriReme Medical, LLC, Pleasanton, CA (US)

( * ) Notice: Subject to any disclaimer, the term of this patent is extended or adjusted under 35 U.S.C. 154(b) by 56 days.

(21) Appl. No.: 14/941,480

(22) Filed: Nov. 13, 2015

(65) Prior Publication Data
US 2016/0136397 A1    May 19, 2016

Related U.S. Application Data

(60) Provisional application No. 62/080,831, filed on Nov. 17, 2014.

(51) Int. Cl.
*A61M 25/10* (2013.01)
*A61B 17/22* (2006.01)

(52) U.S. Cl.
CPC . *A61M 25/104* (2013.01); *A61B 2017/22061* (2013.01); *A61M 2025/105* (2013.01);
(Continued)

(58) Field of Classification Search
CPC ........ A61M 25/104; A61M 2025/1075; A61M 2025/105; A61M 2025/1084;
(Continued)

(56) References Cited

U.S. PATENT DOCUMENTS 2,701,559 A   2/1955 Cooper
2,854,983 A   10/1958 Baskin
(Continued)

FOREIGN PATENT DOCUMENTS

CN    1568165 A    1/2005
EP    0 565 796    10/1993
(Continued)

OTHER PUBLICATIONS

Cambridge University Engineering Department's Materials Data Book, 2003 edition, available online May 5, 2017 at http://www-mdp.eng.cam.ac.uk/web/library/enginfo/cueddatabooks/materials.pdf.*
(Continued)

*Primary Examiner* — Amber Stiles
(74) *Attorney, Agent, or Firm* — Knobbe Martens Olson & Bear LLP (57) ABSTRACT

A system for dilating a stenosed vessel is provided. The system includes a balloon mounted on a catheter shaft, the balloon being composed of a first material and fibers forming a grid attached to a surface of the balloon or integrated within a wall thereof. The fibers are composed of a second material having less elasticity than the first material such that when the balloon is inflated beyond a predetermined pressure balloon regions protrude from the grid formed by the fibers.

28 Claims, 9 Drawing Sheets

(52) U.S. Cl.
CPC ............. *A61M 2025/1031* (2013.01); *A61M 2025/1075* (2013.01); *A61M 2025/1084* (2013.01); *A61M 2025/1086* (2013.01); *A61M 2025/1088* (2013.01)

(58) Field of Classification Search
CPC .. A61M 2025/1086; A61M 2025/1088; A61M 2025/1031; A61B 2017/22061; A61F 2/958
See application file for complete search history.

(56) References Cited

U.S. PATENT DOCUMENTS

| | | |
|---|---|---|
| 3,045,677 A | 7/1962 | Wallace |
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,637,396 A | 1/1987 | Cook |
| 4,723,549 A | 2/1988 | Wholey et al. |
| 4,796,629 A | 1/1989 | Grayzel |
| 4,921,484 A | 5/1990 | Hillstead |
| 4,976,711 A | 12/1990 | Parins et al. |
| 4,998,539 A | 3/1991 | Delsanti |
| 5,071,407 A | 12/1991 | Porter et al. |
| 5,100,386 A | 3/1992 | Inoue |
| 5,133,732 A | 7/1992 | Wilkor |
| 5,176,693 A | 1/1993 | Pannek |
| 5,181,911 A | 1/1993 | Shturman |
| 5,190,058 A | 3/1993 | Jones et al. |
| 5,196,024 A | 3/1993 | Barath |
| 5,222,971 A | 6/1993 | Willard et al. |
| 5,224,945 A | 7/1993 | Pannek, Jr. |
| 5,263,963 A | 11/1993 | Garrison et al. |
| 5,308,356 A | 5/1994 | Blackshear, Jr. et al. |
| 5,320,634 A | 6/1994 | Vigil et al. |
| 5,336,178 A | 8/1994 | Kaplan |
| 5,336,234 A | 8/1994 | Vigil et al. |
| 5,344,419 A | 9/1994 | Spears |
| 5,449,372 A | 9/1995 | Schmaltz et al. |
| 5,456,666 A | 10/1995 | Campbell et al. |
| 5,456,667 A | 10/1995 | Ham et al. |
| 5,460,607 A | 10/1995 | Miyata et al. |
| 5,484,411 A * | 1/1996 | Inderbitzen ....... A61M 25/1002 604/103.08 |
| 5,501,694 A | 3/1996 | Ressemann et al. |
| 5,527,282 A | 6/1996 | Segal |
| 5,556,408 A | 9/1996 | Farhat |
| 5,562,620 A | 10/1996 | Klein et al. |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,628,746 A | 5/1997 | Clayman |
| 5,628,755 A | 5/1997 | Heller et al. |
| 5,643,210 A | 7/1997 | Iacob |
| 5,643,312 A | 7/1997 | Fischell et al. |
| 5,695,469 A | 12/1997 | Segal |
| 5,702,410 A | 12/1997 | Klunder et al. |
| 5,713,863 A | 2/1998 | Vigil et al. |
| 5,730,698 A | 3/1998 | Fischell et al. |
| 5,733,303 A | 3/1998 | Israel et al. |
| 5,735,816 A | 4/1998 | Lieber et al. |
| 5,755,781 A | 5/1998 | Jayaraman |
| 5,772,681 A | 6/1998 | Leoni |
| 5,776,181 A | 7/1998 | Lee et al. |
| 5,797,935 A | 8/1998 | Barath |
| 5,810,767 A | 9/1998 | Klein |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,904,679 A | 5/1999 | Clayman |
| 5,906,639 A | 5/1999 | Rudnick et al. |
| 5,919,200 A | 7/1999 | Stambaugh et al. |
| 5,961,490 A | 10/1999 | Adams |
| 5,967,984 A | 10/1999 | Chu et al. |
| 5,987,661 A | 11/1999 | Peterson |
| 6,013,055 A | 1/2000 | Bampos et al. |
| 6,036,689 A | 3/2000 | Tu et al. |
| 6,036,708 A | 3/2000 | Sciver |
| 6,053,913 A | 4/2000 | Tu et al. |
| 6,059,810 A | 5/2000 | Brown et al. |
| 6,059,811 A | 5/2000 | Pinchasik et al. |
| 6,077,298 A | 6/2000 | Tu et al. |
| 6,102,904 A | 8/2000 | Vigil et al. |
| 6,106,548 A | 8/2000 | Roubin et al. |
| 6,129,706 A | 10/2000 | Janacek |
| 6,156,265 A | 12/2000 | Sugimoto |
| 6,190,403 B1 | 2/2001 | Fischell et al. |
| 6,206,910 B1 | 3/2001 | Berry et al. |
| 6,217,608 B1 * | 4/2001 | Penn .................. A61F 2/82 623/1.15 |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,261,319 B1 | 7/2001 | Kveen et al. |
| 6,309,414 B1 | 10/2001 | Rolando et al. |
| 6,319,251 B1 | 11/2001 | Tu et al. |
| 6,334,871 B1 | 1/2002 | Dor et al. |
| 6,361,545 B1 | 3/2002 | Macoviak et al. |
| 6,416,539 B1 | 7/2002 | Hassdenteufel |
| 6,454,775 B1 | 9/2002 | Demarais et al. |
| 6,540,722 B1 | 4/2003 | Boyle et al. |
| 6,605,107 B1 | 8/2003 | Klein |
| 6,616,678 B2 | 9/2003 | Nishtala et al. |
| 6,626,861 B1 | 9/2003 | Hart et al. |
| 6,652,548 B2 | 11/2003 | Evans et al. |
| 6,656,351 B2 | 12/2003 | Boyle |
| 6,695,813 B1 | 2/2004 | Boyle et al. |
| 6,702,834 B1 | 3/2004 | Boylan et al. |
| 6,939,320 B2 | 9/2005 | Lennox |
| 6,942,680 B2 | 9/2005 | Grayzel et al. |
| 7,186,237 B2 | 3/2007 | Meyer et al. |
| 7,357,813 B2 | 4/2008 | Burgermeister |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,753,907 B2 | 7/2010 | DiMatteo et al. |
| 7,803,149 B2 | 9/2010 | Bates et al. |
| 7,931,663 B2 | 4/2011 | Farnan et al. |
| 8,172,793 B2 | 5/2012 | Bates et al. |
| 8,257,305 B2 | 9/2012 | Speck et al. |
| 8,388,573 B1 | 3/2013 | Cox |
| 8,439,868 B2 | 5/2013 | Speck et al. |
| 9,179,936 B2 | 11/2015 | Feld et al. |
| 9,199,066 B2 | 12/2015 | Konstantino et al. |
| 9,216,033 B2 | 12/2015 | Feld et al. |
| 9,375,328 B2 | 6/2016 | Farnan |
| 9,415,140 B2 | 8/2016 | Speck |
| 9,649,476 B2 | 5/2017 | Speck et al. |
| 2002/0010489 A1 | 1/2002 | Grayzel et al. |
| 2003/0023200 A1 | 1/2003 | Barbut et al. |
| 2003/0040790 A1 | 2/2003 | Furst |
| 2003/0078606 A1 | 4/2003 | Lafontaine et al. |
| 2003/0114915 A1 | 6/2003 | Mareiro et al. |
| 2003/0114921 A1 | 6/2003 | Yoon |
| 2003/0153870 A1 | 8/2003 | Meyer et al. |
| 2003/0195609 A1 | 10/2003 | Berenstein et al. |
| 2004/0034384 A1 | 2/2004 | Fukaya |
| 2004/0073284 A1 * | 4/2004 | Bates .................. A61F 2/82 623/1.11 |
| 2004/0143287 A1 | 7/2004 | Konstantino et al. |
| 2004/0210235 A1 * | 10/2004 | Deshmukh .......... A61F 2/958 606/108 |
| 2004/0210299 A1 | 10/2004 | Rogers et al. |
| 2004/0230293 A1 | 11/2004 | Yip et al. |
| 2005/0021071 A1 | 1/2005 | Konstantino et al. |
| 2005/0125053 A1 | 6/2005 | Yachia et al. |

(56) References Cited

U.S. PATENT DOCUMENTS

| | | | |
|---|---|---|---|
| 2005/0271844 A1 | 12/2005 | Mapes et al. | |
| 2006/0008606 A1 | 1/2006 | Horn et al. | |
| 2006/0015133 A1 | 1/2006 | Grayzel et al. | |
| 2006/0085025 A1 | 4/2006 | Farnan et al. | |
| 2006/0259005 A1 | 11/2006 | Konstantino et al. | |
| 2006/0271093 A1* | 11/2006 | Holman | A61F 2/958 606/194 |
| 2007/0073376 A1 | 3/2007 | Krolik et al. | |
| 2007/0173923 A1 | 7/2007 | Savage et al. | |
| 2008/0255508 A1 | 10/2008 | Wang | |
| 2009/0036964 A1 | 2/2009 | Heringes et al. | |
| 2009/0038752 A1* | 2/2009 | Weng | A61M 25/10 156/276 |
| 2009/0105686 A1 | 4/2009 | Snow et al. | |
| 2009/0192453 A1 | 7/2009 | Wesselman | |
| 2009/0227949 A1 | 9/2009 | Knapp et al. | |
| 2009/0240270 A1 | 9/2009 | Schneider et al. | |
| 2009/0319023 A1 | 12/2009 | Hildebrand et al. | |
| 2010/0042121 A1 | 2/2010 | Schnieder et al. | |
| 2010/0234875 A1* | 9/2010 | Allex | A61M 25/104 606/194 |
| 2010/0331809 A1* | 12/2010 | Sandhu | A61F 2/945 604/500 |
| 2011/0071616 A1 | 3/2011 | Clarke et al. | |
| 2011/0172698 A1 | 7/2011 | Davies et al. | |
| 2012/0059401 A1* | 3/2012 | Konstantino | A61F 2/958 606/159 |
| 2012/0083733 A1* | 4/2012 | Chappa | A61M 25/10 604/103.02 |
| 2012/0245607 A1 | 9/2012 | Gershony et al. | |
| 2013/0046237 A1 | 2/2013 | Speck et al. | |
| 2013/0116655 A1 | 5/2013 | Bacino et al. | |
| 2013/0190725 A1* | 7/2013 | Pacetti | A61M 25/10 604/509 |
| 2013/0211381 A1 | 8/2013 | Feld | |
| 2013/0218181 A1 | 8/2013 | Feld et al. | |
| 2014/0066960 A1 | 3/2014 | Feld et al. | |
| 2015/0209556 A1* | 7/2015 | Timothy | A61M 25/104 606/192 |
| 2016/0022968 A1 | 1/2016 | Feld et al. | |
| 2016/0058991 A1 | 3/2016 | Feld et al. | |
| 2016/0100964 A1 | 4/2016 | Feld et al. | |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| JP | 2005-508709 | 4/2005 |
| WO | WO 98/05377 | 2/1998 |
| WO | WO 98/50101 | 11/1998 |
| WO | WO 2002/068011 | 9/2002 |
| WO | WO 2003/041760 | 5/2003 |
| WO | WO 2005/020855 | 3/2005 |
| WO | WO 2011/112863 | 9/2011 |
| WO | WO 2013/114201 | 8/2013 |
| WO | WO 2013/119735 | 8/2013 |

OTHER PUBLICATIONS

Plastics Materials, J. A., Brydson, sixth edition, 1995, p. 510, available in part online on May 5, 2017 at https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false.*

Plastics Materials, J. A., Brydson, sixth edition, 1995, p. 510, available in relevant part online on Aug. 21, 2017 at https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false.*

Cambridge University Engineering Department's Materials Data Book, 2003 edition, available online Aug. 21, 2017 at http://www-mdp.eng.cam.ac.uk/web/library/enginfo/cueddatabooks/materials.pdf.*

Bearing Works, (PTFE) Polytetrafluoroethylene material specifications sheet, available online Feb. 11, 2018 at https://www.bearingworks.com/uploaded-assets/pdfs/retainers/ptfe-datasheet.pdf.*

Plastics Materials, J. A., Brydson, sixth edition, 1995, p. 510, available in part online on Feb. 12, 2018 at https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false.*

Plastics Materials, J. A., Brydson, sixth edition, 1995, p. 510, available in relevant part online on Jun. 12, 2018 at https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false.*

Cambridge University Engineering Department, Materials Data Book, 2003 edition, available online Jun. 12, 2018 at http://www-mdp.eng.cam.ac.uk/web/library/enginfo/cueddatabooks/materials.pdf.*

AngioSculpt XL PT Scoring Balloon Catheter Brochure, AngioScore, Inc., Rev. C, May 2013.

Kadish, A., et al. "Mapping of Atrial Activation With a Noncontact, Multielectrode Catheter in Dogs," *Circulation: Journal of the American Heart Association*, (Apr. 1999) 99: 1906-1913.

International Search Report for Appl. No. PCT/IB2015/058802, dated Feb. 5, 2016 in 17 pages.

* cited by examiner

BALLOON CATHETER SYSTEM AND METHOD OF USING SAME

INCORPORATION BY REFERENCE TO ANY PRIORITY APPLICATIONS

This application claims priority benefit under 35 U.S.C. § 119(e) of U.S. Provisional Application No. 62/080,831, filed Nov. 17, 2014, the entirety of which is incorporated by reference herein.

BACKGROUND

Field

The present disclosure relates to a balloon catheter system and method for treating biological vessels and, more particularly, to an angioplasty balloon catheter which includes a grid of fibers attached to, or integrated within a wall of the balloon. The fibers are less elastic than the balloon material and as such, when the balloon is inflated beyond a predetermined pressure a plurality of balloon regions protrude from the grid formed by the fibers.

Description of the Related Art

Percutaneous transluminal angioplasty (PTA) is a procedure in which a balloon catheter is inserted through an artery and guided to the region of lumen narrowing. The balloon is inflated to force the plaque material (typically fat and calcium) against the wall of the artery to open the vessel lumen and improve blood flow.

Angioplasty balloons are typically cylindrical when inflated and have different lengths and diameters to conform to different vessel sizes. The balloons are inflated at high pressure, normally between 8-20 atmospheres, in order to overcome the resistance of the plaque and achieve luminal expansion.

Standard balloons (also referred to as plain balloons) are the most commonly used technique for dilation of a lesion in a blood vessel (angioplasty); however, standard balloons suffer from several disadvantages.

Since the diameter and composition of stenotic regions of an artery are not typically uniform, inflation of a standard balloon in a vessel leads to non-uniform (axially and radially) expansion. Variability in the lesion composition (lesions can be composed of a mixture of hard and soft plaque material) will lead to variability in resistance to dilation along the lesion and to balloon over expansion in the least resistant regions of the vessel. As a result, standard balloons can apply excessive forces to less resistant regions of the lesion thus traumatizing the vessel wall (e.g. dissections) and yet do not apply enough forces to resistant plaque regions to enable effective dilation thereof.

Trauma to the vessel wall is associated with poor long term clinical results and can accelerate or induce restenosis in the treated areas. In addition, major dissections, such as flow limiting dissections require stenting further complicating the procedure.

Attempts to solve the aforementioned limitations of standard balloon catheters by increasing forces on resistant plaque region via cutting or scoring elements (blades/wires) positioned on the balloon surface (e.g. U.S. Publication No. 20040143287 and U.S. Publication No. 20060085025) were somewhat successful but did not adequately solve problems resulting from non-uniform balloon expansion. In addition, cutting and scoring balloons are not designed to avoid traumatizing the vessel walls, but instead to control the trauma to the vessel walls by inducing controlled and predictable dissections.

Thus, there is a need for a high pressure angioplasty balloon catheter capable of effectively opening resistant plaque regions without traumatizing the vessel walls in less resistant plaque regions.

SUMMARY

According to one aspect of the present disclosure, there is provided a system for dilating a stenosed vessel comprising: (a) a balloon mounted on a catheter shaft, the balloon being composed of a first material; and (b) a plurality of fibers forming a grid attached to a surface of the balloon or integrated within a wall thereof, the plurality of fibers being composed of a second material having less elasticity than the first material such that when the balloon is inflated beyond a predetermined pressure a plurality of balloon regions protrude from the grid formed by the plurality of fibers.

According to further features of the disclosure described below, the balloon is composed of a first polymer, and the plurality of fibers are composed of a second polymer.

According to still further features in the described embodiments, a thickness of each of the plurality of fibers is selected from a range of 10-750 microns.

According to still further features in the described embodiments, a thickness of each of the plurality of fibers varies along its length.

According to still further features in the described embodiments, the grid forms a plurality of cells having an area selected from a range of 1-25 mm2.

According to still further features in the described embodiments, the grid is attached to a surface of the balloon via an adhesive.

According to still further features in the described embodiments, the grid is attached to a surface of the balloon via welding.

According to still further features in the described embodiments, a tensile modulus of each of the plurality of fibers is selected from a range of 1-150 GPa and the tensile modulus of the balloon is selected from a range of 0.0002-0.0100 GPa.

According to still further features in the described embodiments, the cells include triangular or diamond-shaped cells or both.

According to still further features in the described embodiments, a lead angle of the cells is selected from a range of 30-180 degrees.

According to still further features in the described embodiments, a linear mass density of each of the plurality of fibers is 1-100 Denier.

According to still further features in the described embodiments, a linear mass density of each of the plurality of fibers is 50 Denier.

According to still further features in the described embodiments, the grid pattern is formed from N fibers helically wound around the balloon in a clockwise direction and N fibers helically wound around the balloon in a counterclockwise direction. The balloon can optionally include L longitudinal fibers, wherein L can be 2 or more.

According to still further features in the described embodiments, N is selected from a range of 4-16.

According to still further features in the described embodiments, N is 4.

According to still further features in the described embodiments, the predetermined pressure is at least 2 atmospheres.

According to still further features in the described embodiments, the plurality of isolated balloon regions protrude at least 0.1 mm from the surface when the balloon is inflated to its working pressure (e.g. 5-25 ATMs).

According to still further features in the described embodiments, the grid is sandwiched between the balloon and a layer of material.

According to still further features in the described embodiments, each of the plurality of fibers is a monofilament fiber.

According to still further features in the described embodiments, each of the plurality of fibers is a multifilament fiber.

According to still further features in the described embodiments, each of the plurality of fibers is composed of polypropylene, PLLA, PEEK, aramids (Kevlar®), polyester fibers (Dacron®), aromatic polyesters (Vectran®), aliphatic polyamides (nylons) and/or ultra-high molecular weight polyethylene.

According to still further features in the described embodiments, the balloon and/or the plurality of fibers are coated with a drug-containing formulation.

According to still further features in the described embodiments, the drug is an antiproliferative drug.

The present disclosure successfully addresses the shortcomings of the presently known configurations by providing a balloon catheter system, which can be used to open stenosed vessels without traumatizing the vessel wall.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods, and materials are described below. In case of conflict, the patent specification, including definitions, will control. In addition, the materials, methods, and examples are illustrative only and not intended to be limiting.

BRIEF DESCRIPTION OF THE DRAWINGS

The disclosure is herein described, by way of example only, with reference to the accompanying drawings. With specific reference now to the drawings in detail, it is stressed that the particulars shown are by way of example and for purposes of illustrative discussion of the embodiments of the present disclosure only, and are presented in the cause of providing what is believed to be the most useful and readily understood description of the principles and conceptual aspects of the disclosure. In this regard, no attempt is made to show structural details of the disclosure in more detail than is necessary for a fundamental understanding of the disclosure, the description taken with the drawings making apparent to those skilled in the art how the several forms of the disclosure may be embodied in practice.

DETAILED DESCRIPTION

The present disclosure relates to a balloon catheter system, which is capable of applying uniform pressure to a vessel wall even under high inflation pressures and as such can be used to dilate stenosed regions of a body vessel such as an artery while applying a uniform expansion force to all portions of the treated vessel.

The principles and operation of the present disclosure may be better understood with reference to the drawings and accompanying descriptions.

Before explaining at least one embodiment of the disclosure in detail, it is to be understood that the disclosure is not limited in its application to the details set forth in the following description or exemplified by the Examples. The disclosure is capable of other embodiments or of being practiced or carried out in various ways. Also, it is to be understood that the phraseology and terminology employed herein is for the purpose of description and should not be regarded as limiting.

In a previously filed patent application (U.S. Publication No. 20140066960, filed Aug. 21, 2013, the entire disclosure of which is hereby incorporated by reference), the disclosure described an angioplasty balloon catheter having an expandable constraining structure positioned over a balloon. The expandable constraining structure is not attached to the balloon but is expanded thereby to constrain balloon inflation and enable isolated balloon regions to protrude from the constraining structure during inflation. This ensures that the balloon applies a uniform force on the vessel wall when inflated and reduces the likelihood of dissections and other trauma.

Although experiments have shown that the balloon catheter of U.S Publication No. 20140066960 is highly effective in dilating stenosed regions and minimizing trauma to the vessel wall, due to its metal constraining structure it has a fairly large packing diameter and limited flexibility and maneuverability through torturous vessels.

In order to traverse these limitations, the present inventors have devised a balloon catheter which is capable of providing the benefits of U.S. Publication No. 20140066960 under high inflation pressures, is easy to manufacture and can be efficiently packed for delivery while being highly maneuverable through torturous vessels. As is further described hereinbelow, such benefits are provided by a fiber grid which is attached to, or integrated into the balloon wall and is configured for modifying the shape of the balloon surface to form pillow-like protrusions upon balloon inflation.

Balloons with integrated or attached fiber grids are known in the art (e.g. U.S. Publication No. 20060271093 or U.S. Publication No. 20050271844). However, such fiber grids are utilized to prevent balloon over-inflation and increase balloon integrity under high inflation pressures and not for modifying the shape of the inflated balloon to form pillow-like balloon protrusions through the grid.

Thus, according to one aspect of the present disclosure, there is provided a system for dilating a stenosed vessel. As used herein, the term vessel refers to any hollow conduit in the body and includes blood vessels such as arteries and veins, lymphatic vessels, GI tract vessels (e.g. intestines), ducts and any body passage, which conducts a biological fluid. As is further described hereinunder, one preferred use of the present system is in angioplasty of arteries such as peripheral (e.g. leg) arteries.

The present system includes a balloon composed of a first material (e.g. first polymer) mounted on a catheter shaft and a plurality of fibers forming a grid-like pattern attached to a surface of the balloon or integrated within a wall thereof. The fibers are composed of a second material (e.g. second polymer) which is preferably stronger and less stretchable than the first material.

As such, inflation of the balloon beyond a predetermined threshold pressure (e.g. above 3 ATMs) stretches the balloon material more than the fibers, forming channels along the balloon surface where the fibers are constrained or fixed and balloon protrusions therebetween where the balloon material is unconstrained. The grid of fibers maintains balloon uniformity (axially and radially) throughout inflation enabling the protrusions (also referred to herein as pillows) to uniformly contact the vessel wall and plaque material thus ensuring uniform force distribution along the treated vessel region and minimizing vessel trauma while effectively dilating the entire plaque region. In addition, since the channels formed by the grid fibers are recessed from the vessel wall when the balloon is inflated, they provide stress relief regions and further reduce the likelihood of trauma.

In order to enable formation of the protrusions and control protrusion height area and shape, one must carefully select the balloon and fiber material, the strength and diameter of the fibers and the shape of the grid formed thereby.

The balloon material is selected based on desired compliance (defined herein as elasticity or tensile modulus) and resistance to rupture (strength). The fiber is selected based on strength and elasticity.

The catheter shaft can be any configuration suitable for use in the desired procedure. For example, in angioplasty procedures the catheter can be configured for over-the-wire or a rapid exchange delivery and can include suitable connectors for wire insertion, inflation and the like at its proximal end. The catheter shaft can be any length and diameter suitable for angioplasty of peripheral, coronary, or cerebral blood vessels. Suitable length (L) and diameter (D) of the balloon can be in the range of about 4-40 mm L, 1.25-5 mm D for coronary applications and 20-300 mm L, 2-12 (or more) mm D for peripheral vessels applications.

The balloon can be a compliant or a semi-compliant balloon fabricated from polyamide, Pebax, polyurethane, polyethylene terephthalate, or similar material and the like at dimensions selected from a range of about 5-300 mm in length and about 2-12 (or more) mm in diameter. The balloon can be cylindrical or any other shape known in the art. For example, when utilized in angioplasty, the balloon can be roughly cylindrical in shape with tapered ends with a length of 5-300 mm and a diameter of 2-12 mm the taper is normally similar or slightly shorter than the balloon diameter. The elasticity of the balloon material can be between 0.0002 to 0.0100 GPa.

The grid can be formed from single filament or multi-filament fibers (of the same or different filaments) that are woven or braided from any material suitable for such purposes. The fibers can be 10-750 microns in thickness, such as in the radial direction, with uniform or variable thickness throughout fiber length (over balloon). For example, the fiber can be thicker at the balloon tapers or legs and thinner at the working length.

The fibers can be made from various polymers (such as polyurethane, polyamide, polyethylene or other) or metals (such as Nitinol or Cobalt chromium alloy or other) or composites thereof, other suitable material. Specific and preferred examples include ultra-high molecular weight polyethylene, polyvinylidene fluoride, and polyethylene terephthalate. A presently preferred material for the fibers is ultra-high molecular weight polyethylene.

Multifilament fibers are typically measured in units of Deniers, which is a unit of measure for the linear mass density of fibers. The linear mass density of the fibers can be 10-100 Deniers, preferably 50 deniers.

The elasticity of the fibers can range from 0.1-500 GPa, preferably 100 GPa.

Braid density of the fibers is also important and is determined by the picks per inch (PPI), i.e. the number of fiber crossovers per inch of balloon length; a high PPI correlates with a high burst pressure. The PPI used to fabricate the grid of the present system is preferably within a range of 2-20, more preferably 6-14.

Several approaches can be used to fabricate the present system. The present system is assembled while the balloon is an inflated or semi-inflated form under a pressure of 0.3-20 ATMs (preferably 0.3-8 ATMs, more preferably 0.3-2 ATMs). The inflation pressure used sets the extent of balloon material stretching which in turn determines the outer diameter of the constrained segment of the balloon and maximum protrusion height of the isolated balloon regions of a fully inflated balloon.

When the balloon is not inflated (or is inflated to a pressure below the threshold), the fiber braid protrudes from the surface of the balloon (FIG. 3b) or is formed with the balloon surface (when sandwiched between two layers of balloon wall material) such that the balloon wall does not extend radially outwardly beyond the fiber braid. When inflated to a pressure above the threshold pressure, the isolated balloon regions protrude from the braid openings to a height that is defined as the distance between the surface of the braid fiber and outermost surface of the isolated balloon regions (arrow, FIG. 3c). Such a height can be at least about 0.1 mm, and in some implementations at least about 0.1 or 0.2 or more, at the nominal inflated working pressure. In general, the height will be within the rage of from about 0.01-1 mm or 0.1-0.5 mm.

In a 3 mm balloon (which is capable of reaching diameters greater than 3 mm with over inflation), assembly of the fibers is effected over a balloon inflated to about 3 mm in diameter. When the assembled balloon is inflated inside a vessel, protrusions of the isolated balloon regions will for at this diameter, and will gradually increase in height along with inflation. At 3.5 mm in diameter, the height of the isolated balloon regions protruding from the balloon surface will begin at 3.5 mm and gradually increase in height with inflation, typically to about 0.01-0.5 mm in increased height.

The fibers are preferably attached to the balloon surface along the entire length of each fiber. Attachment is effected using an adhesive applied to the fibers or by sandwiching the fibers between two adhesive layers applied to the balloon surface, a base and cover adhesive layer. These layers can be applied via dipping, spraying, or any other approach known in the art. The base layer of the balloon wall can be any flexible adhesive layer that allows for immobilization of the fibers but retains the flexibility of the underlying balloon substrate while the cover layer further immobilizes the grid, protects it from the vessel wall and plaque and enhances vascular wall-gripping.

A smooth cover layer is particularly advantageous when the present balloon catheter is utilized for dilating in-stent restenosis. The cover layer of the present balloon prevents 'stent jailing'—a phenomenon in which struts of, for example, cutting/scoring balloons, are trapped within stent struts.

Attachment or partial-attachment of the fibers to the balloon surface may be desirable in order to maintain fiber position over the balloon throughout inflation, and thus maintain the shape and size of the isolated balloon regions. If the fibers were free to move the uniformity of balloon protrusions could not be maintained and thus uniform vessel dilation would not be possible. Fixation of the fibers in a specific grid shape is also very important over the balloon tapers where a free wire would tend to slip from its intended position more easily, again resulting in protrusion non-uniformity.

The fibers are braided over the balloon working length at a lead angle as defined by the PPI. The angle can vary from 30-180 degrees. In one embodiment, each isolated balloon region (protruding between channels) is surrounded by four crossing fibers angled at approximately 90 degrees to each other. Since the lead angle is constant and equal for all fibers, the isolated balloon regions formed between the fibers are square/rectangle. At this configuration, the fibers are positioned to resist tension forces applied thereupon by the pressure buildup in the balloon.

In the above example, the fibers are braided lengthwise and radially, however, the present grid can also be formed by helical braiding of fibers over the working length and tapers of the balloon.

An optional top layer can be applied to the balloon following sandwiching of the fiber grid between the base and cover layers. This top layer decreases the tackiness of the balloon and improves its ability to track through a tortuous anatomy and inflate within the vessel site. The top layer can be composed of parylene or any other material commonly known in the art.

Alternatively, the balloon can be coated with a coating following sandwiching of the fiber grid between the base and cover layers. This coating can be a hydrophilic material or a hydrophobic material. The coating decreases the tackiness of the balloon and improves its ability to track through a tortuous anatomy and inflate within the vessel site. The top layer can be composed of silicone, polyurethane, polyvinylpyrrolidone, hyaluronic acid, or any other material commonly known in the art.

When assembled the balloon can be folded in regular folding techniques known in the art. The balloon can be folded to 2-8 pleats, with the pleats being wrapped around the balloon axis as done with plain balloon. The fibers are soft enough to allow such folding.

One specific embodiment of manufacturing process is described hereinbelow:

(i) The balloon is inflated, preferably to 0.3-2 ATMs.
(ii) A polyurethane adhesive is applied to the base layer of the balloon via spraying, dipping, or painting.
(iii) The adhesive base layer is cured and the fibers are braided over the balloon surface. A variable pitch process is used over the legs, tapers, and working length with a PPI range over the working length of 6-14.
(iv) A cover layer of polyurethane adhesive is applied over the braided grid to fix the fibers in place and ensure a continuous fiber coating to minimize interaction between fibers and plaque material.
(v) The adhesive cover layer is cured and an optional outer layer is applied to the balloon to minimize tackiness and enhance delivery to a vessel site.

FIGS. 1-4 illustrate one embodiment of the present balloon system, which is referred to herein as system 10. System 10 is configured for use in angioplasty procedures.

Figure 1:
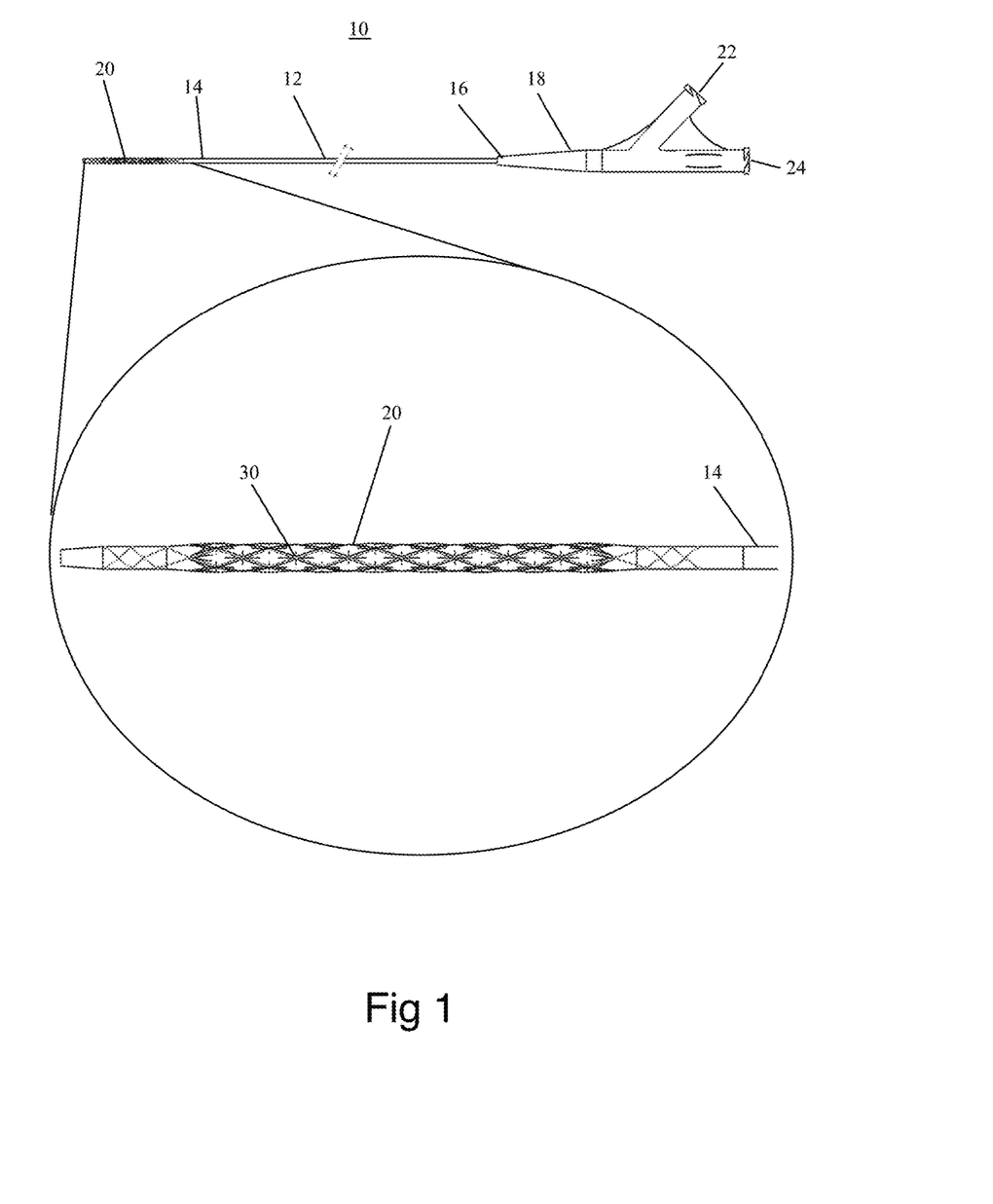
FIG. 1 is a side view of a catheter including the present balloon and a magnified view of the balloon portion of the catheter.

System 10 includes a catheter shaft 12, which is fabricated from polymer extrusions and includes longitudinal lumens running the length of shaft 12. A first lumen can accommodate a guidewire while a second lumen can serve as an inflation conduit for balloon 20 mounted on a distal portion 14 of shaft 12. Proximal portion 16 of shaft 12 includes a connector 18 having dedicated ports 22 and 24 communicating with the second and first lumens (respectively).

Figure 2:
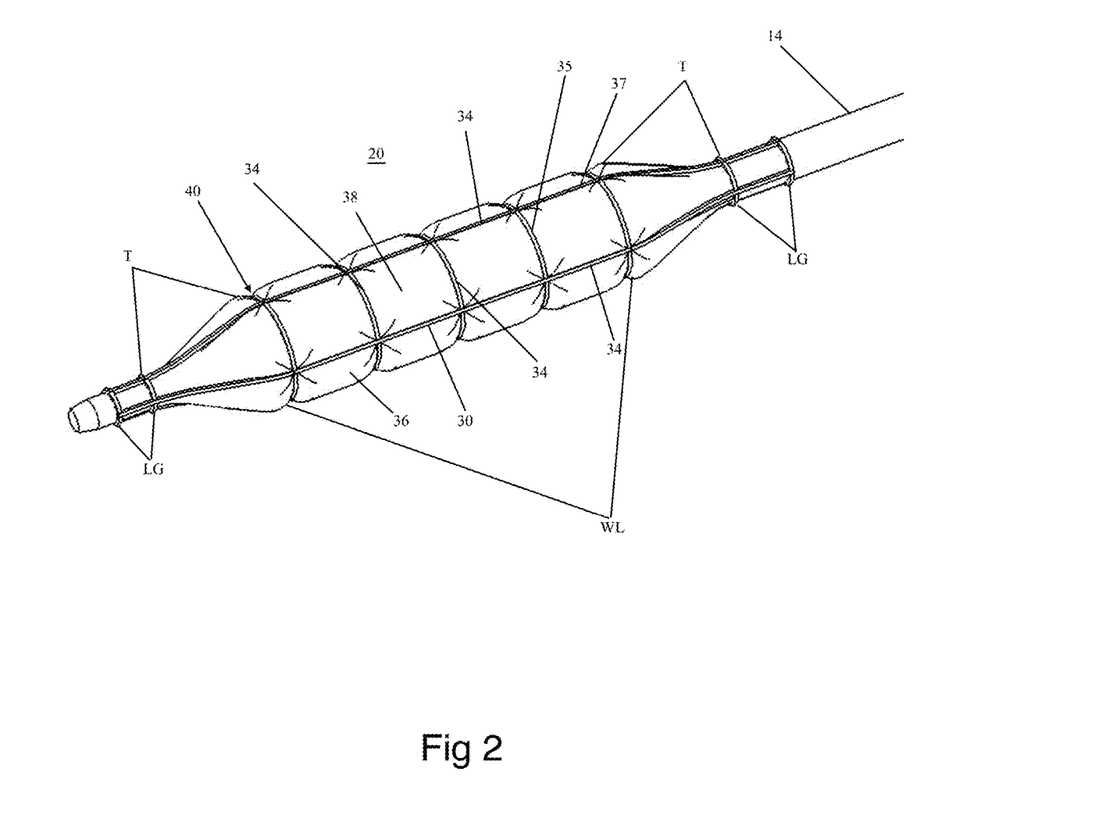
FIG. 2 is an isometric view of an inflated balloon including a grid having square-shaped openings.

For coronary applications balloon 20 can be between 1.25 to 5.0 mm in diameter and 4 to 40 mm in length (when inflated as shown in FIG. 2). For peripheral applications, balloon 20 can be between 2 to 12 mm in diameter and 5 to 300 mm in length. A longer balloon may taper (radially) along its length. The wall thickness of balloon 20 can vary from 1-250 µm (variable depending on material and specified characteristics). The balloon wall thickness can be uniform or variable.

Balloon 20 is attached to distal portion 14 of shaft 12 using approaches well known in the art (e.g. gluing or welding). A grid 30 is integrated into, or glued onto wall 32 of balloon 20 as is described above. Grid 30 is formed from two or more fibers 34 (five radial fibers 35 and four axial fibers 37 shown in FIG. 2) that are braided/woven over the length of balloon 20 including working length (WL), legs (LG) and tapers (TP).

As is shown in FIG. 2, when balloon 20 is inflated to nominal pressure (e.g. 6-20 ATMs), grid 30 enables isolated balloon regions 36 to protrude through openings 38 formed between fibers 34 and form channels 40 in the balloon surface. Depending on several variables in construction of balloon 20 and grid 30 including balloon and fiber material, grid shape and density and the like, isolated balloon regions 36 can protrude 0.01-0.5 mm from the balloon surface. The grid 30 can include a number of circumferential fiber portions intersecting a number of axial fiber portions. In general, there can be about 3 to about 20 circumferential fiber portions, such as about 4 to about 10 circumferential fiber portions, and about 3 to about 10 axial fiber portions, such as about 3 to about 5 axial fiber portions. In some implementations, there can be about 10 to about 20 isolated balloon regions, such as about 12 to about 18 balloon regions or about 14 to about 16 balloon regions.

As is mentioned herein, isolated balloon regions 36 contact the plaque in the vessel and apply a uniform force thereto, while channels 40 (which are recessed from the plaque) function as stress relief regions.

Figure 3A:
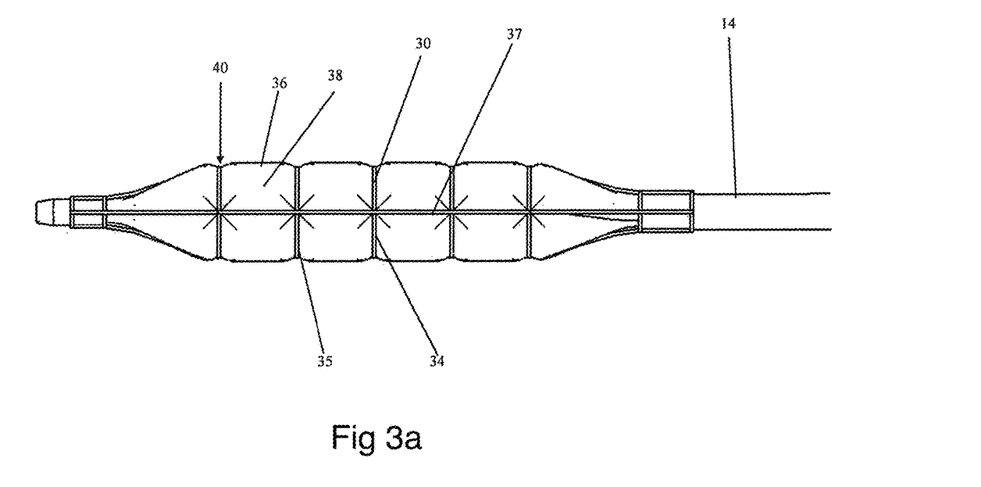
FIG. 3a is a side view of the balloon of FIG. 2.
Figure 3B:
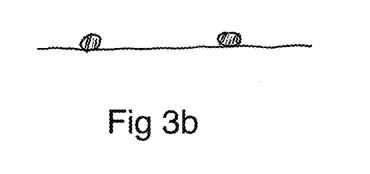
FIGS. 3b and 3c illustrate the balloon surface and braid of a deflated balloon or a balloon inflated up to a predetermined threshold (FIG. 3b) and inflated beyond the threshold (FIG. 3c) balloon.
Figure 3C:
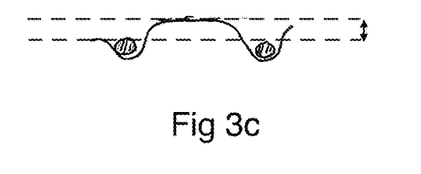
Figure 4:
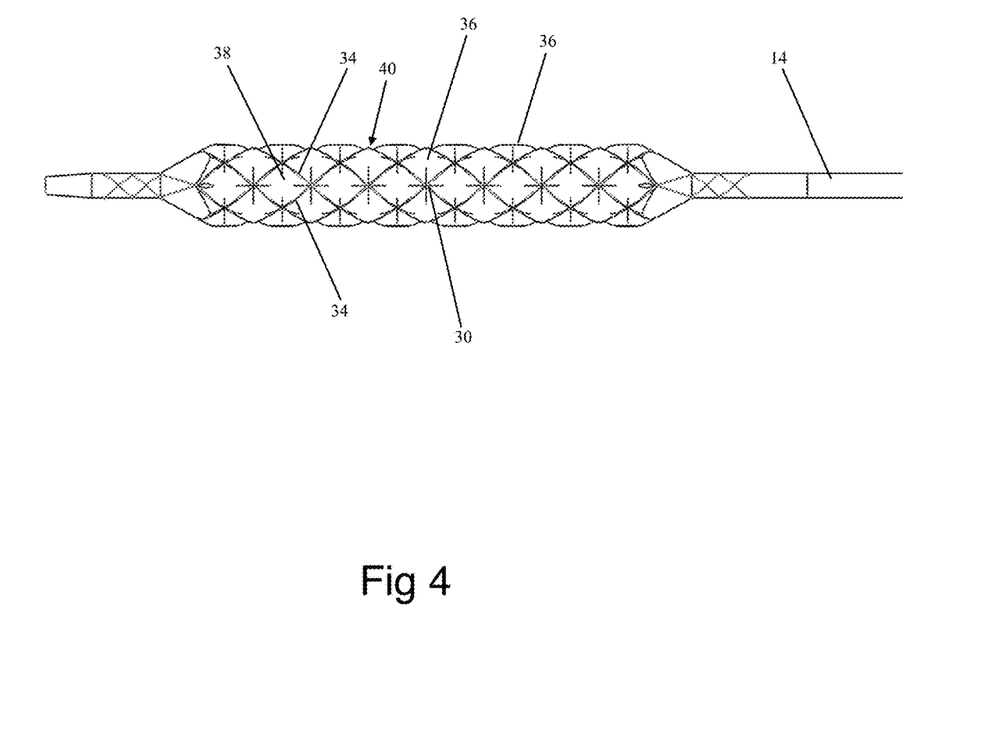
FIG. 4 is a side view of an inflated balloon including a grid having diamond-shaped openings.
Figure 5:
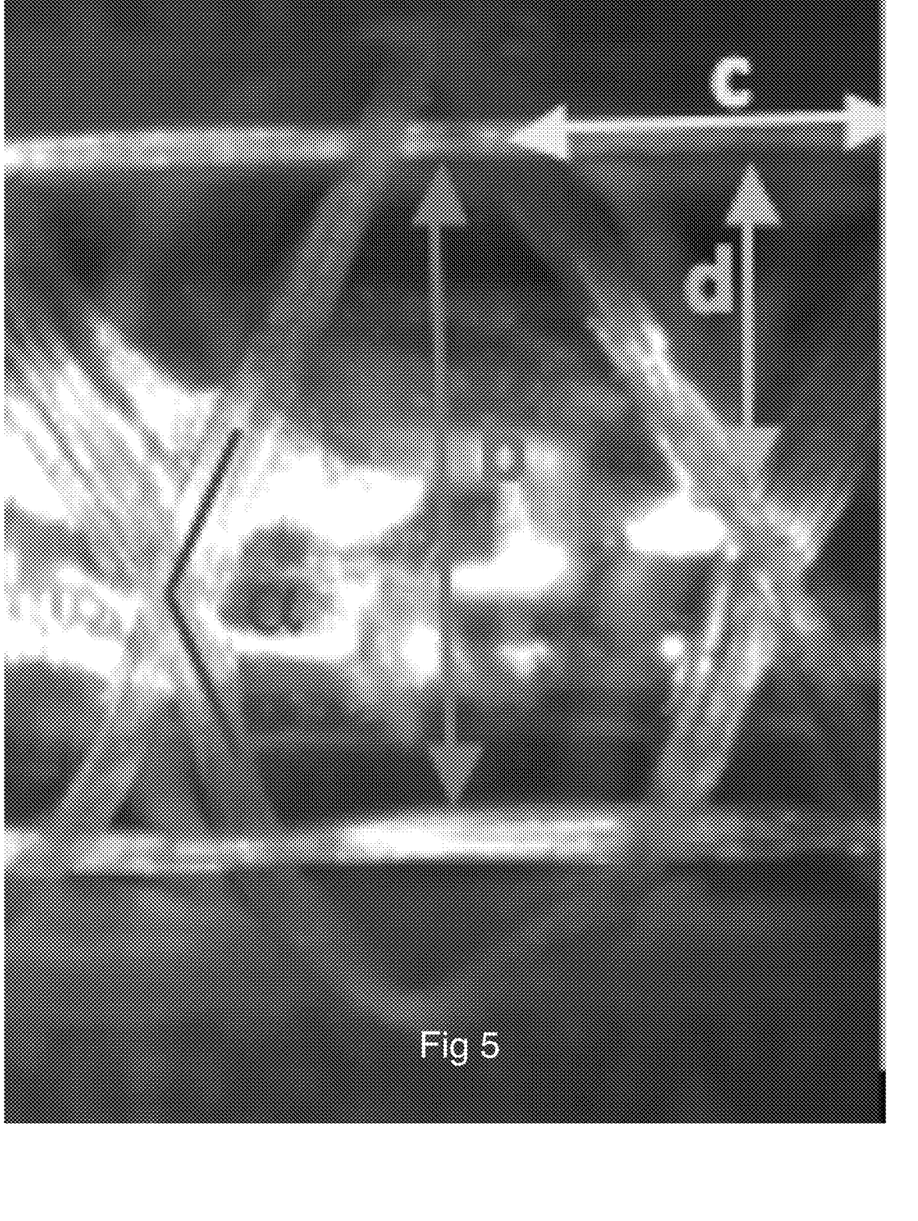
FIG. 5 is an image illustrating an angle and distances of importance between fibers of a balloon prototype constructed according to the teachings of the present disclosure.
Figure 6A:
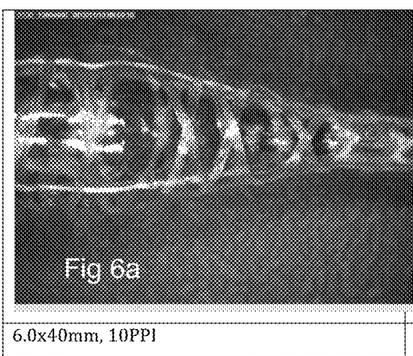
FIGS. 6a-6d illustrate a 6×40 mm balloon braided at 6 (FIG. 6b, 6d) or 10 (FIGS. 6a, 6c) PPI showing the balloon tapered end (FIGS. 6a, 6b) and center portion (FIGS. 6c, 6d).
Figure 6B:
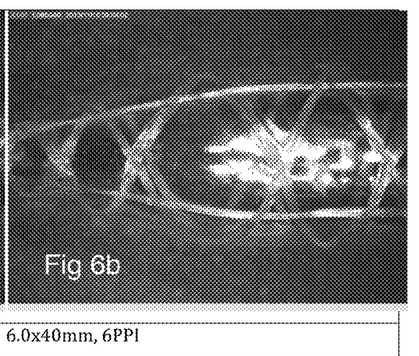
Figure 6C:
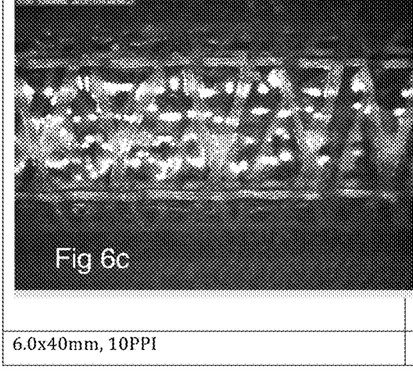
Figure 6D:
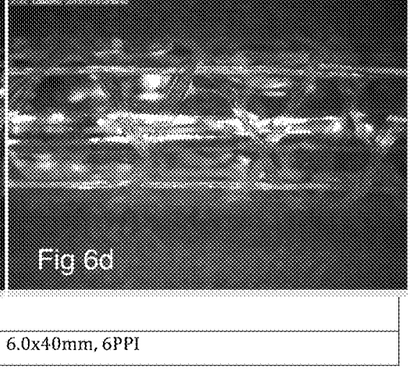

Four to seventy two fibers can be positioned around balloon 20 depending on the length and diameter thereof. Fibers 34 can be laid down in any pattern as long as the grid formed thereby includes openings 38 of roughly the same area and shape. For example, fibers 34 can be laid down longitudinally (axially) and radially to form square or rectangular openings 38 (as is shown in FIGS. 2-3), or fibers 34 can be helically wound clockwise and counterclockwise to form diamond-shaped openings 38 as is shown in FIG. 4 which illustrates a grid 30 formed from helically wound fibers 34. A combination of these two approaches can also be used by providing axial fibers to limit balloon elongation and form triangular-shaped openings 38 (FIG. 5).

The number of fibers 34 correlates to the density of the braid forming the grid and the number of and area of openings 38 (forming isolated balloon regions 36).

In one embodiment of the present disclosure shown in FIGS. 6a-d, a balloon 20 that is 40 mm in length and 6.0 mm in diameter includes a braided grid 30 formed from 8 fibers 34, 4 longitudinal fibers 34 and 4 radially wound fibers 34. This braiding pattern forms triangular and hexagonal-shaped isolated balloon regions 3 when inflated.

Figure 8:
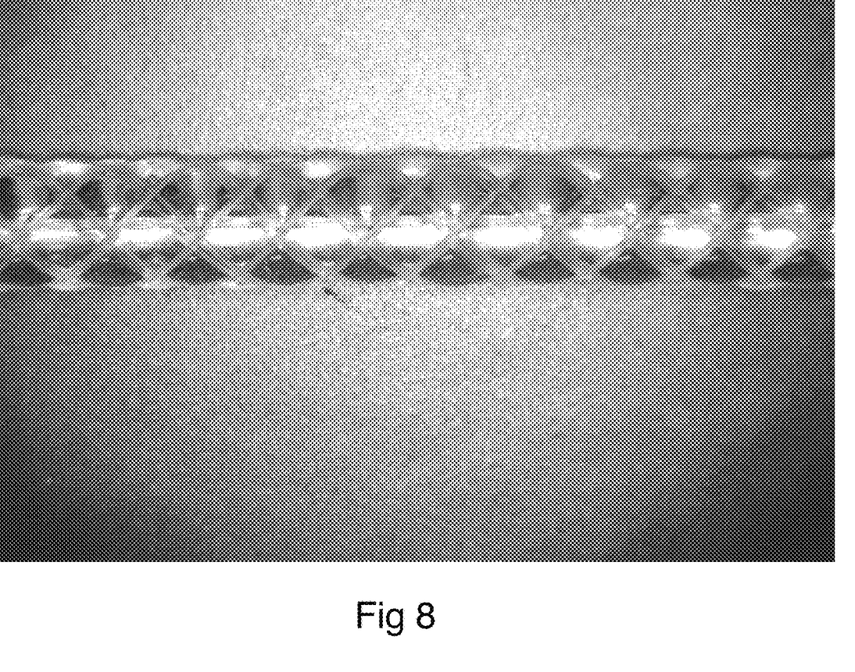
FIG. 8 is a balloon braided with a diamond pattern.
Figure 9:
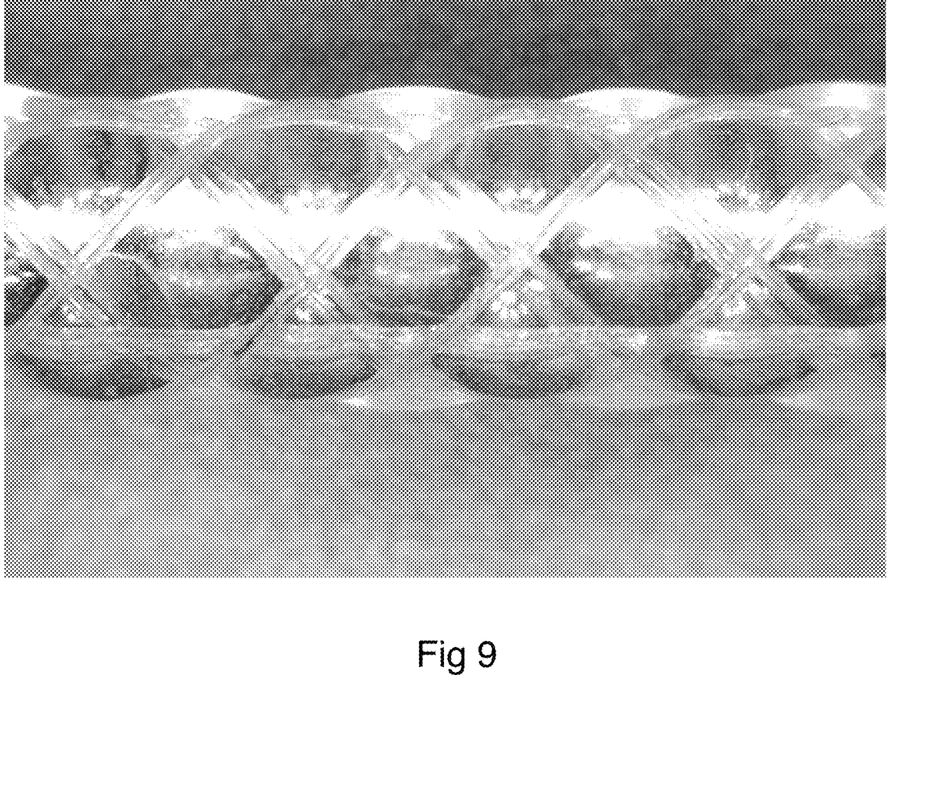
FIG. 9 is a close up of the balloon of FIG. 8.

In another embodiment of the present disclosure shown in FIGS. 8-9, balloon 20 can include helical (H)+longitudinal (L) fibers 34 (wherein the number of H fibers is greater than the number of L fibers), with L fibers longitudinally arranged around the balloon, H/2 fibers 34 helically wrapped clockwise and H/2 fibers 34 helically wrapped counterclockwise. This result in a grid 30 forming triangular and hexagonal-shaped openings 38 through which isolated balloon regions 36 protrude around the circumference of balloon 20.

The total number of isolated balloon regions 36 depends on the balloon length: In the example of FIG. 3a, isolated balloon regions 36 are defined by a square with a diagonal length of $3\times\pi/4=2.35$ mm. As a result, every 2.35 mm of balloon 20 length will include $2\times4=8$ isolated balloon regions 36. A $3\times20$ mm balloon will therefore include $8\times20/2.35=68$ isolated balloon regions 36.

Grid 30 preferably has a variable pitch (fiber 34 angles) over the working length (WL), legs (LG), and tapers (TP) of balloon 20 (FIG. 2). Such variation can accommodate for changes in balloon 20 diameters over its length (e.g. taper expands less than working length) or can alter the local compliance of a balloon region (e.g. make a taper region less compliant).

System 10 can be used in angioplasty as follows. System 10 can be guided to the stenosed region over a guide-wire (not shown) using well known angioplasty approaches. Once in position, balloon 20 can be inflated to a point where it channels 40 and isolated balloon regions 36 are formed to apply an outward radial force to the plaque at isolated balloon regions 36 and stress relief regions at channels 40. Once the region is sufficiently dilated, balloon 20 is deflated and system 10 is removed from the body.

Thus, the present disclosure provides a balloon system, which protects the vessel wall from uneven expansion, as well as enables provision of localized higher pressure forces to specific lesion regions that are resistant, such as highly calcified expansion-resistant plaque regions.

Balloon 20 of system 10 and/or grid 30 can be coated with a hydrophilic or hydrophobic coating to enhance lubricity or coated with a drug composition containing, for example, an antiproliferative drug such as sirolimus or paclitaxel using methods well known in the art.

As used herein the term "about" refers to ±10%.

Additional objects, advantages, and novel features of the present disclosure will become apparent to one ordinarily skilled in the art upon examination of the following examples, which are not intended to be limiting.

EXAMPLES

Reference is now made to the following examples, which together with the above descriptions, illustrate the disclosure in a non-limiting fashion.

Bench Testing of Braided Balloons

Several prototype balloons were constructed according to the teachings of the present disclosure and tested as described below.

Briefly, a nylon balloon was fabricated via blow molding and the balloon was pre-inflated to 0.3 atm. The balloon was dip-coated in a polyurethane adhesive and an ultra-high molecular weight polyethylene multifilament fiber was braided in a diamond pattern over the balloon surface. The balloon was then dip-coated in a second layer of the polyurethane adhesive followed by dip-coating in parylene. FIGS. 8 and 9 illustrate an inflated balloon prototype with a diamond braiding pattern. The balloons were dried and folded to determine the folded diameter.

Figure 7A:
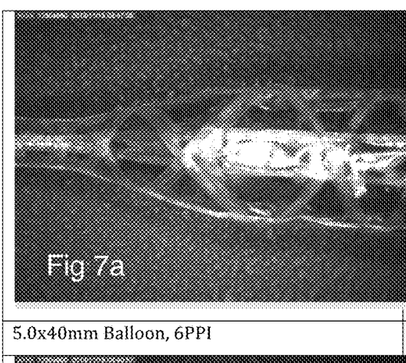
FIGS. 7a-7d illustrate a 5×40 mm balloon braided at 6 (FIG. 7a, 7c) or 10 (FIGS. 7b, 7d) PPI showing the balloon tapered end (FIGS. 7a, 7b) and center portion (FIGS. 7c, 7d).
Figure 7B:
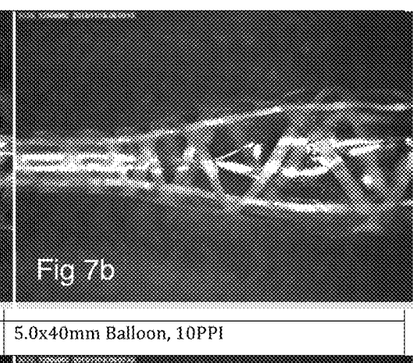
Figure 7C:
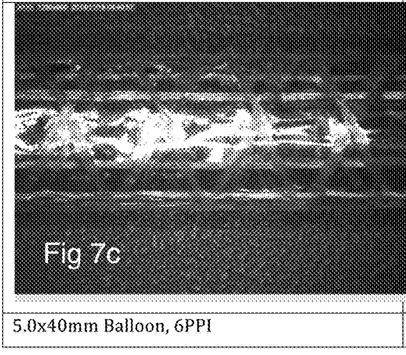
Figure 7D:
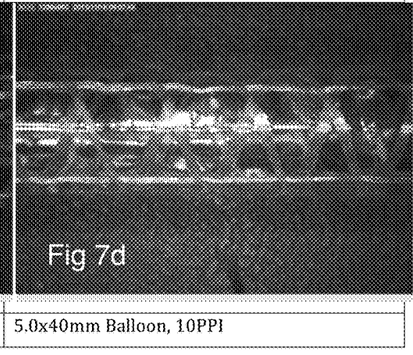

Five types of balloons were constructed, a 6 mm (inflated diameter)×40 mm (inflated length) balloon at two PPI densities of 6, 10 (FIGS. 6a-6d) and a 5 mm×40 mm balloon at three PPI densities of 6, 10 and 14 (FIGS. 7-7d, PPI 14 not shown).

The following parameters were tested for each balloon type:

(i) compliance—diameter of the balloon as a function of pressure;
(ii) burst pressure—measurement of the pressure at which the balloon material fails;
(iii) fatigue—measurement of the number of repeated inflation-deflation cycles before the balloon material fails; and
(iv) profile—measurement of the diameter of the folded balloon.

Table 1 below summarizes the results with the 5 tested balloons.

TABLE 1

| | | Pillow Height | | Burst(atm) | | Dia @ 8 atm (mm) | | Dia @ 8 atm (mm) | | | | | |
|---|---|---|---|---|---|---|---|---|---|---|---|---|---|
| Size | PPI | 8 atm (mm) | 12 atm (mm) | Balloon Only | Braided Balloon | Balloon Only | Braided Balloon | Balloon Only | Braided Balloon | ☐☐ ☐deg) | b (mm) | c (mm) | d (mm) |
| 6.0 × 40 | 6 | N/A | N/A | 16.40 | 24.25 ± 0.07 | 6.70 | 6.40 ± 0.00 | 7.10 | 6.65 ± 0.07 | 125.5 | 4.3 | 2.6 | 2.3 |
| 6.0 × 40 | 10 | 0.18 | 0.26 | | 27.60 ± 4.10 | | 6.30 ± 0.10 | | 6.47 ± 0.06 | 142 | 4.2 | 1.7 | 1.9 |
| 5.0 × 40 | 6 | 0.31 | 0.41 | 17.2 | 24.65 ± 0.78 | 5.70 | 5.43 ± 0.15 | 6.20 | 5.67 ± 0.21 | 125.5 | 3.85 | 2.5 | 2.2 |
| 5.0 × 40 | 10 | 0.29 | 0.39 | | 29.75 ± 2.19 | | 5.33 ± 0.15 | | 5.47 ± 0.06 | 141 | 3.65 | 1.4 | 2.4 |
| 5.0 × 40 | 14 | 0.16 | 0.26 | | 41.20 ± 2.83 | | 5.10 | | 5.20 | N/A | N/A | N/A | N/A | a-d are shown in FIG. 5 and denote the following:
a-(alpha) is the angle of intersection for the fibers as marked in the drawing
b- is the distance between longitudinal fibers
c- is the length of longitudinal fiber as marked in the drawing
d- is the distance as marked in the drawing It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

Although the disclosure has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure.

What is claimed is:

1. A system for dilating a stenosed vessel comprising:
   a balloon mounted on a catheter shaft, said balloon being composed of a first material; and
   a plurality of fibers forming a grid, the grid extending an entire length of the balloon, each of said plurality of fibers being glued or welded to a wall of said balloon along the entire length of said fiber, said plurality of fibers being composed of a second material having less elasticity than said first material such that when said balloon is inflated beyond a predetermined pressure a plurality of balloon regions protrude from said grid formed by said plurality of fibers,
   wherein the system is configured to transition to an inflated configuration in which the plurality of balloon regions protrude from said grid and then transition to a deflated configuration in which the balloon and the plurality of fibers are removed, and
   wherein prior to inflation, both the balloon and the plurality of fibers are folded and wrapped around an axis of the balloon.

2. The system of claim 1, wherein said balloon is composed of a first polymer and said plurality of fibers are composed of a second polymer.

3. The system of claim 2, wherein a tensile modulus of each of said plurality of fibers is selected from a range of 1-150 GPa and said tensile modulus of said balloon is selected from a range of 0.0002-0.0100 GPa.

4. The system of claim 1, wherein a thickness of each of said plurality of fibers is selected from a range of 10-750 microns.

5. The system of claim 1, wherein a thickness of each of said plurality of fibers varies along its length.

6. The system of claim 1, wherein said grid forms a plurality of cells each having an area selected from a range of 1-25 mm$^2$.

7. The system of claim 6, wherein said cells include triangular and diamond-shaped cells.

8. The system of claim 6, wherein a lead angle of said cells is selected from a range of 30-180 degrees.

9. The system of claim 1, wherein a linear mass density of each of said plurality of fibers is 1-100 Denier.

10. The system of claim 1, wherein a linear mass density of each of said plurality of fibers is 50 Denier.

11. The system of claim 1, wherein said grid is formed from N fibers helically wound around said balloon in a clockwise direction and N fibers helically wound around said balloon in a counterclockwise direction.

12. The system of claim 11, wherein N is selected from a range of 4-16.

13. The system of claim 11, wherein N is 4.

14. The system of claim 11, further comprising longitudinal fibers crossing the N fibers helically wound around said balloon in a clockwise direction and crossing the N fibers helically around said balloon in a counterclockwise direction.

15. The system of claim 1, wherein said predetermined pressure is at least 2 atmospheres.

16. The system of claim 1, wherein said plurality of balloon regions protrude at least 0.1 mm from a surface of said grid.

17. The system of claim 1, wherein said grid is sandwiched between said balloon and a layer of material.

18. The system of claim 1, wherein each of said plurality of fibers is a monofilament fiber.

19. The system of claim 1, wherein each of said plurality of fibers is a multifilament fiber.

20. The system of claim 1, wherein each of said plurality of fibers is composed of polypropylene, PLLA, PEEK, Kevlar, and/or ultra high molecular weight polyethylene.

21. The system of claim 1, wherein said balloon and/or said plurality of fibers are coated with a drug-containing formulation.

22. The system of claim 21, wherein said drug is an antiproliferative drug.

23. The system of claim 1, wherein when said balloon is inflated beyond the predetermined pressure, the plurality of balloon regions uniformly protrude from said grid.

24. A system for dilating a stenosed vessel comprising:
   a balloon mounted on a catheter shaft, said balloon being composed of a first material; and
   a plurality of fibers forming a grid, the grid extending an entire length of the balloon, each of said plurality of fibers being glued or welded to a wall of said balloon along the entire length of said fiber, said plurality of fibers being composed of a second material having less elasticity than said first material such that when said balloon is inflated beyond a predetermined pressure a plurality of balloon regions protrude from said grid formed by said plurality of fibers, the second material being pliable,
   wherein prior to inflation, both the balloon and the plurality of fibers are folded and wrapped around an axis of the balloon.

25. The system of claim 24, wherein said balloon is coated with a drug-containing formulation.

26. The system of claim 24, wherein said plurality of fibers are coated with a drug-containing formulation.

27. The system of claim 24, further comprising longitudinal fibers crossing the N fibers helically wound around said balloon in a clockwise direction and crossing the N fibers helically around said balloon in a counterclockwise direction.

28. The system of claim 24, wherein when said balloon is inflated beyond the predetermined pressure, the plurality of balloon regions uniformly protrude from said grid.

* * * * *